United States Patent [19]

Horodysky

[11] Patent Number: 4,618,437

[45] Date of Patent: Oct. 21, 1986

[54] MULTIFUNCTIONAL FRICTION-MODIFYING ADDITIVES AND COMPOSITIONS THEREOF

[75] Inventor: Andrew G. Horodysky, Cherry Hill, N.J.

[73] Assignee: Mobil Oil Company, New York, N.Y.

[21] Appl. No.: 750,195

[22] Filed: Jul. 1, 1985

[51] Int. Cl.$^4$ ............... C10M 129/00; C10M 137/00; C10M 139/00
[52] U.S. Cl. ................................ 252/32.5; 252/47.5; 252/49.6; 252/49.9; 548/110; 548/347
[58] Field of Search .................... 252/49.9, 32.5, 49.6, 252/47.5; 548/110, 347

[56] References Cited

U.S. PATENT DOCUMENTS

| | | | |
|---|---|---|---|
| 3,920,567 | 11/1975 | Miller | 252/32.5 |
| 4,298,486 | 11/1981 | Horodysky et al. | 252/49.6 |
| 4,478,732 | 10/1984 | Horodysky et al. | 548/110 |
| 4,532,056 | 7/1985 | Horodysky et al. | 252/49.6 |
| 4,557,844 | 12/1985 | Horodysky | 252/49.6 |

Primary Examiner—William R. Dixon, Jr.
Assistant Examiner—Cynthia A. Prezlock
Attorney, Agent, or Firm—Alexander J. McKillop; Michael G. Gilman; Howard M. Flournoy

[57] ABSTRACT

Boronated internal imidazoline acid phosphates provide effective friction reducing characteristics for lubricant compositions when incorporated therein.

25 Claims, No Drawings

MULTIFUNCTIONAL FRICTION-MODIFYING ADDITIVES AND COMPOSITIONS THEREOF

BACKGROUND OF THE INVENTION

This invention is directed to lubricant compositions containing small additive concentrations of reaction products which possess excellent multifunctional activity. This invention is also directed to such additives as novel compositions of matter.

The need for friction reducing modifiers in lubricating oils to meet the ever changing requirements of modern engines is well known. Various materials and various techniques have been proposed.

Imidazolines are well known for their lubricity properties and for their antirust and corrosion-inhibiting properties when formulated into lubricating oils and for their water scavenging and antirust characteristics when blended into fuels.

The use of phosphorus containing lubricating additives has also found widespread use. Phosphonates have been found to be lubricity and antiwear agents as exemplified by U.S. Pat. No. 4,356,097 which describes the use of hydrocarbyl phosphonates in lubricant formulations.

U.S. Pat. No. 4,478,732 describes imidazoline salts of acid phosphates and U.S. Pat. No. 4,318,817 describes phosphate acid esters as corrosion inhibitors in functional fluid such as hydraulic oils. U.S. Pat. No. 4,505,830 is drawn to $C_{10}$-$C_{20}$ alkyl substituted imidazoline salts of boric acid or phosphoric acid as useful in metal working lubricants. The use of boron-containing lubricating additives is broadly disclosed by U.S. Pat. Nos. 4,406,806, 4,478,732; 4,440,656; 4,406,802 and numerous publications.

SUMMARY OF THE INVENTION

In accordance with the present invention the use of novel boronated zwitterionic (internal) acid phosphate salts of imidazolines in lubricants provides effective antifriction activity. Furthermore these unique boron-containing imidazoline-derived acid phosphates provide more effective friction reducing and antiwear activity than acid imidazolines that have been previously reported in the prior art. The exceptional benefits of these novel additives, coupled with the imidazoline moiety, apparently provide the basis for the significant synergistic antiwear activity.

These benefits are also expected for a variety of synthetic and mineral oil-based lubricants. These additives are useful as multifunctional additives in oils of lubricating viscosity, greases prepared therefrom and liquid hydrocarbyl or hydrocarbyloxy fuels.

DESCRIPTION OF THE PREFERRED EMBODIMENTS

The imidazolines defined herein are generally prepared by reacting a suitable imidazoline with phosphorous pentoxide and thereafter reacting the resulting phosphate acid salt with an appropriate boronating agent. The imidazolines in accordance with the present invention therefore may be prepared by the following generalized reaction:

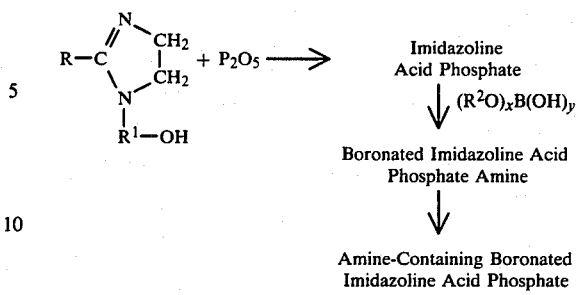

R is about $C_6$ to about $C_{30}$ hydrocarbyl and can additionally contain oxygen, sulfur and/or nitrogen. $R^1$ is from about $C_1$ to about $C_6$ hydrocarbylene and $R^2$ is from $C_1$ to about $C_6$ hydrocarbyl.

The imidazolines can be formed by the reaction of various carboxylic acids or mixtures thereof with appropriate hydroxyalkylamines. Suitable acids include oleic, stearic, isostearic, tallowacids, decanoic acid and similar fatty acids.

The imidazoline acid phosphates prepared as described above and reacted with a suitable boronating agent form boronated imidazoline acid phosphates which may then be further reacted with an amine to yield amine containing boronated imidazoline acid phosphates.

The boronating agents include but are not limited to boric acid, trialkyl borates, metaborates, and boron oxides and other suitable organic or inorganic boron sources.

Amines useful include hydrocarbyl amines, such as oleylamine, stearylamine, tallowamine, alkoxylated amines, hydrocarbyl diamines such as N-oleyl-1,3-propylenediamine or triamines, imidazolines, amine-containing polyisobutyenyl-succinimides, and the like.

Less than molar quantities of phosphorus pentoxide and the boronating agent can also be used and less than molar quantities of nitrogenous base can be used when the amine containing boronated acid phosphates are prepared.

A mixture of products is believed to form during the imidazoline-phosphorus pentoxide boronation reactions. At least a portion is believed to contain the boron-containing internal imidazoline acid phosphate salt described herein. To obtain the amine-containing product generally less than molar quantities of a suitable amine is reacted at about 50°–100° C. with the boronated imidazoline-derived acid phosphate. The imidazoline-derived products may contain 0.001%–10% boron and 0.01%–10% phosphorus.

All of the reactants may be obtained commercially or they may be prepared by any process of reaction known to the art. Preparation of the products in accordance herewith is preferably carried out in the desired two stages or steps. In the first stage the imidazoline is reacted with $P_2O_5$ preferably in less than molar quantities producing an imidazoline acid phosphate which is then reacted preferably with less than molar quantities of a boronating agent to product the internal boron-containing imidazoline acid phosphate. Boric acid or a trialkyl borate are preferable. Reaction temperatures in the first step may range from about 50° to about 120° C. and in the second step, they may range from 50° to about 150° C. or more. The overall reaction can accordingly be carried out at temperatures of from about 90° to about 180° C. Solvents preferably can be used in either reaction step such as hydrocarbon solvents and include toluene, xylene, heptane and the like.

The additives embodied herein are useful in lubricating oil and greases (or liquid hydrocarbyl or hydrocarbyloxy fuels) in an amount which imparts significant friction modifying/antiwear characteristics to the oil, thereby reducing the friction of an engine operating with the oil in its crank case. Concentrations of about 0.01 to about 10 wt.% based on the total weight of the composition are normally used. Preferably, the concentration is from about 0.1 to about 3 wt.%.

Of particular significance in accordance with the present invention is the ability to improve both the antiwear characteristics and friction reducing characteristics of oleaginous materials such as hydrocarbyl lubricating media which may comprise liquid oils in a form of either a mineral oil or a synthetic oil, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F., and preferably, from about 50 to about 250 SSU at 210° F. These oils may have viscosity indexes ranging to about 100 or higher. Viscosity indexes from about 70 to about 95 are preferred. The average molecular weights of these oils may range from about 250 to about 800.

Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, such as lithium or calcium stearates or hydroxy stearates which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which are normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include, but are not limited to, polyisobutylene, polybutenes, hydrogenated polydecenes, polypropylene glycol, polyethylene glycol, trimethylolpropane esters, neopentyl and pentaerythritol esters, di(2-ethylhexyl)sebacate, di(2-ethylhexyl)adipate, dibutyl phthalate, fluorocarbons, silicate esters, silanes, esters of phosphorus-containing acids, liquid, ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl)ether, phenoxy phenylethers.

It is to be understood, however, that the compositions contemplated herein can also contain other materials. For example, corrosion inhibitors, extreme pressure agents, viscosity index improvers, co-antioxidants, other antiwear agents and the like can be used. Included are metallic phenates or sulfonates, metallic phosphorodithioates polysuccinimides and the like. These materials do not detract from the value of the compositions of this invention, rather the materials serve to impart their customary properties to the particular compositions in which they are incorporated.

The following examples illustrate the invention. They are illustrative only and are not meant to limit it.

EXAMPLE 1

Boron-Containing Acid Phosphate of Hydroxyalkyl Alkenylimidazoline

Step A—Approximately 700 g of 2-(1-hydroxyethyl)-1-heptadecenylimidazoline (commercially obtained as Amine O) and 100 g n-hexane was charged to a glass reactor and heated to 70° C. Over a 2-hour period of time, 20 g phosphorus pentoxide was added. The temperature was then held at 110° C. for 2 hours and 130° C. for 2 hours. The solvent was vacuum topped at 130° C. to remove volatiles. The intermediate was filtered hot through diatomaceous earth.

Step B—Approximately 175 g of the above product, 20 g boric acid, and 100 g toluene was charged to a glass reactor equipped additionally with Dean-Stark tube and condenser. The reactants were heated up to 150° C. until water evolution during azeotropic distillation ceased. The solvent was removed by vacuum distillation and the product was filtered through diatomaceous earth. The product contained Boron 18500 ppm
Nitrogen 6.8 wt.%

EXAMPLE 2

Boron-Containing Acid Phosphate of Hydroxyalkyl Alkenylimidazoline.

Step A≦Approximately 350 g of 2-(1-hydroxyethyl)-1-heptadecylimidazoline (commercially obtained as Amine O) and 50 g n-hexane was charged to a glass reactor and heated to 70° C. Over a 2-hour period of time, 20 g phosphorus pentoxide was added. The temperature was then held at 110° C. for 2 hours and 130° C. for 2 hours. The solvent was vacuum topped at 130° C. to remove volatiles. The intermediate was filtered hot through diatomaceous earth.

Step B—Approximately 175 g of the above product, 20 g boric acid, and 100 g toluene was charged to a glass reactor equipped additionally with Dean-Stark tube and condenser. The reactants were heated up to 150° C. until water evolution during azeotropic distillation ceased. The solvent was removed by vacuum distillation and the product was filtered through diatomaceous earth. The product contained Boron 18600 ppm
Nitrogen 6.9 wt.%

EXAMPLE 3

Boron-Containing Acid Phosphate of Hydroxyalkyl Alkenylimidazoline

Step A—Approximately 350 g of 2-(1-hydroxyethyl)-1-heptadecylimidazoline (commercially obtained as Amine O) and 50 g n-hexane was charged to a glass reactor and heated to 70° C. Over a 2-hour period of time, 30 g phosphorus pentoxide was added. The temperature was then held at 110° C. for 2 hours and 130° C. for 2 hours. The solvent was vacuum topped at 130° C. to remove volatiles. The intermediate was filtered hot through diatomaceous earth.

Step B—Approximately 175 g of the above product, 20 g boric acid, and 100 g toluene was charged to a glass reactor equipped additionally with Dean-Stark tube and condenser. The reactants were heated up to 150° C. until water evolution during azeotropic distillation ceased. The solvent was removed by vacuum distillation and the product was filtered through diatomaceous earth.

EXAMPLE 4

Alkylamine Reaction Product of Boron-Containing Acid Phosphate of Hydroxyalkyl Alkenyl Imidazoline Approximately 75 g of the product of Example 3 was reacted with 4 g of $C_{11}$–$C_{13}$ t-alkyl amine

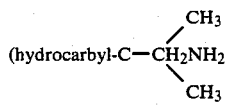

—obtained commercially as Primene 81R from Rohm & Haas) at 70° C. for 1 hour.

The products were blended into fully formulated oils and evaluated for their friction-reducing properties as shown in Table 1.

EVALUATION OF THE REACTION PRODUCTS

The compounds were evaluated in the Low Viscosity Friction Apparatus (LVFA) as shown in Table 1 below. The LVFA and test procedure as described in U.S. Pat. No. 4,252,973.

TABLE 1

| Frictional Characteristics | | |
|---|---|---|
| | | Reduction or % |
| | Additive | Change in |
| | Concen- | Coefficient |
| | tration | of Friction |
| | Wt. % | 5 Ft/Min / 30 Ft/Min |
| Base Oil A (fully formulated synthetic engine oil containing detergent/dispersant/inhibitor performance package) SAE 10W-30 | — | 0 / 0 |
| Example 1 - Boron-Containing Acid Phosphate of Hydroxyalkyl Alkenylimidazoline | 2.0 | 46 / 34 |
| | 1.0 | 29 / 16 |
| Example 2 - Boron-Containing Acid Phosphate of Hydroxyalkyl Alkenylimidazoline | 2.0 | 51 / 48 |
| | 1.0 | 32 / 22 |
| Example 3 - Boron-Containing Acid Phosphate of Hydroxyalkyl Alkenylimidazoline | 2.0 | 26 / 22 |
| Example 4 - t-Alkylamine Reaction Product of Boron-Containing Acid Phosphate of Hydroxyalkyl Alkenyl-imidazoline of Example 3 | 2.0 | 46 / 30 |

The results clearly demonstrate the friction-modifying effectiveness of the compositions in accordance with the invention.

The data disclosed in Table 1 clearly demonstrate the friction-modifying effectiveness of the compositions which contain the internal acid phosphate salts described herein. They are useful at low concentrations, are ashless and do not contain any potentially undesirable sulfur or metallic salts. They may be readily prepared in a two-step one-pot process, comparable in many respects to known reactions currently practiced commercially.

The products were evaluated for antiwear properties using the 4-Ball machine. Example 1 was blended into a fully formulated lubricating fluid. The Shell Four-Ball Wear Test, ASTM D2266, is described in, for example, U.S. Pat. No. 4,434,291.

TABLE 2

| Antiwear Characteristics | | |
|---|---|---|
| Four-Ball Machine Wear Test Test Run for 30 Minutes @ 1500 rpm With 60 kg load @ 175° F. | Additive Condition Wt. % | Wear Scar Diameter, mm |
| Base Oil - 80/20 mixture of 100″ solvent paraffinic bright and 200″ solvent paraffinic neutral lubricating oils | — | 2.0 |
| Example 1 - Boron-Containing Acid Phosphates of Hydroxyalkyl Alkenylimidazoline | 1.0 | 0.6 |

The results clearly show the antiwear performance of Example 1 in accordance with the invention.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A composition comprising a major proportion of an oil of lubricating viscosity or grease prepared therefrom and a minor friction reducing or antiwear proportion of a boronated imidazoline derived internal acid phosphate prepared by reacting a hydrocarbyl imidazoline in the following generalized reaction with phosphorus pentoxide, followed by reaction with a boronating agent

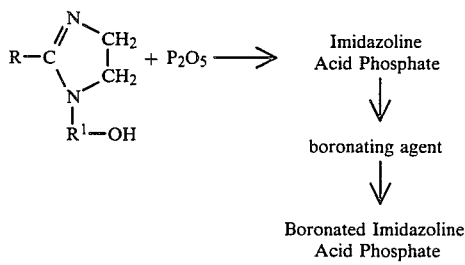

Imidazoline Acid Phosphate

↓ boronating agent

↓

Boronated Imidazoline Acid Phosphate where

R is about $C_6$ to about $C_{30}$ hydrocarbyl or hydrocarbyl substituted with oxygen, sulfur and/or nitrogen and $R^1$ is $C_1$ to about $C_6$ hydrocarbylene.

2. The composition of claim 1 wherein the reaction is carried out at temperatures of from about 50° to about 180° C. with less than molar quantities of phosphorus pentoxide and less than molar quantities of the boronating agent.

3. The composition of claim 2 wherein the reaction with $P_2O_5$ is carried out at temperatures ranging from about 50° to about 120° C.

4. The composition of claim 2 wherein the phosphorus pentoxide is added incrementally to the reaction mixture.

5. The composition of claim 1 wherein the boronating agent is selected from the group consisting essentially of $(R^2O)xB(OH)y$, boron oxides and metaborates and where $R^2$ is from $C_1$ to about $C_6$ hydrocarbyl, x is from 0 to 3 and y is from 0 to 3 with the proviso that $x+y$ must equal 3.

6. The composition of claim 1 wherein the boronating reaction is carried out at temperatures of from about 50° to about 180° C.

7. The composition of claim 5 wherein the boronating agent is selected from the group consisting essentially of boric acid and trialkyl borates.

8. The composition of claim 7 wherein the boronating agent is boric acid.

9. The composition of claim 1 wherein the boronated imidazoline acid phosphate is thereafter reacted with a $C_2$ to about a $C_{32}$ hydrocarbyl amine, diamine, etheramine or etherdiamine to produce an amine-containing boronated internal imidazoline acid phosphate.

10. The composition of claim 1 wherein said major proportion is selected from the group consisting of mineral oils, synthetic oils or mixtures thereof.

11. The composition of claim 10 wherein said major proportion is a mineral oil.

12. The composition of claim 10 wherein said major proportion is a synthetic oil.

13. The composition of claim 10 wherein said major proportion is a grease.

14. A liquid hydrocarbyl or hydrocarbyloxy fuel containing a minor amount of an imidazoline derived internal boronated acid phosphate prepared as set forth in claim 1.

15. The composition of claim 1 wherein said boronated imidazoline acid phosphate is further reacted with a hydrocarbyl amine, diamine, ether amine or ether diamine to produce an amine containing boronated internal acid phosphate.

16. The composition of claim 15 wherein the amine is a $C_{11}$ to $C_{13}$ tertiary alkyl amine.

17. An additive product consisting of an imidazoline derived internal acid phosphate prepared by reacting a hydroxyalkyl hydrocarbyl imidazoline in the following generalized reaction with phosphorus pentoxide, followed by reaction with a boronating agent

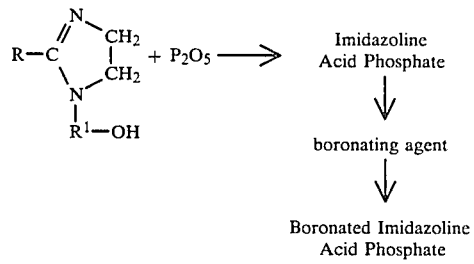

Imidazoline Acid Phosphate

↓ boronating agent

↓

Boronated Imidazoline Acid Phosphate where

R is about $C_6$ to about $C_{30}$ hydrocarbyl or hydrocarbyl substituted with sulfur, oxygen and/or nitrogen, and $R^1$ is $C_1$ to about $C_6$ hydrocarbylene.

18. The additive product of claim 17 wherein the overall reaction is carried out at temperatures of from about 50° to about 180° C. with less than molar quantities of phosphorus pentoxide and boronating agent.

19. The additive product of claim 17 wherein the reaction with phosphorus pentoxide is carried out at a temperature of from about 50° to about 120° C.

20. The additive product of claim 17 wherein the reaction with the boronating agent is carried out at temperatures ranging from about 50° to about 180° C.

21. The additive product of claim 17 wherein the boronating agent is selected from the group consisting essentially of $(R^2O)xB(OH)y$, boron oxides and metaborates and where $R^2$ is from $C_1$ to about $C_6$ hydrocarbyl, x is from 0 to 3, y is from 0 to 3 with the proviso that $x+y$ must equal 3.

22. The process of claim 21 wherein the boronating agent is boric acid.

23. The additive product described in claim 17 wherein the amine is a $C_{11}$ to $C_{13}$ tertiary alkyl amine.

24. The additive product described in claim 17 wherein it is further reacted with a $C_1$ to about a $C_{32}$ hydrocarbyl amine, diamine, etheramine or etherdiamine to produce an amine-containing boronated internal acid phosphate.

25. A method of reducing friction in internal combustion engines and improving fuel consumption thereof by treating the moving parts of said engines with a composition as described in claim 1.

* * * * *